United States Patent [19]

Mark, Jr. et al.

[11] 4,310,400

[45] Jan. 12, 1982

[54] THIN LAYER ELECTRODE AND CELL

[76] Inventors: Harry B. Mark, Jr., 6122 Dryden, Cincinnati, Ohio 45202; Andrzej Czerwinski, c/o Laboratory of Radio Chemistry Dept. Chemistry Warsaw University UL. Zwiarki, Wigury 101, 02-089 Warszawa, Poland; Josip Caja, c/o Chemistry Dept. University of Sagreb, Sagreb, Yugoslavia

[21] Appl. No.: 121,687

[22] Filed: Feb. 26, 1980

[51] Int. Cl.$^3$ .......................................... G01N 27/30
[52] U.S. Cl. ................................................ 204/195 M
[58] Field of Search .......... 204/195 M, 195 L, 195 R, 204/195 B, 195 F, 282, 1 R, 1 T, 296

[56] References Cited

U.S. PATENT DOCUMENTS 3,634,213  1/1972  Coates ............................ 204/296 X
3,657,095  4/1972  Tosteson ......................... 204/195 L
3,743,591  7/1973  Steinhardt ....................... 204/195 L

OTHER PUBLICATIONS

A. T. Hubbard, CRC Critical Reviews in Analytical Chem., pp. 201-241, March 1973.
Chemie Ingenieur Technik, "Perfluorierte Kationenaustauscher-Polymere", Walther Grot, 1975, p. 617.
"Perfluorierte . . . thermischer Stabilitat", Walter Grot, 1972, pp. 167-169.
Simple Electrode for Thin-Layer Electrochemistry", J. C. Schaeffer & D.G. Peters, 1970, pp. 430-432.
"Chronopotentiometry in Thin Layers of Solution", C. R. Christensen & F. C. Anson, 1963, pp. 205-209.
"Conducting Glass Electrode . . . of Neptunium", R. C. Propst, 1971, pp. 994-999.
"Use of Nafion . . . Electrolytic Cells", Walther Grot, 1978, pp. 299-301.
"A New Dip-Type . . . Non-Aqueous Systems", J. E. McClure & D. L. Maricle, 1966, (3 pp.) (no page numbers).
"An Electrochemical . . . Thin Layer Electrode", T. P. DeAngelis & W. R. Heineman, 1976, pp. 594-597.
"Thin-Layer Coulometry: . . . Oxide Stoichiometry", J. M. LeCuire & Y. Pillet, 1978, pp. 99-106.

Primary Examiner—G. L. Kaplan
Attorney, Agent, or Firm—Wood, Herron & Evans

[57] ABSTRACT

A thin layer electrolytic cell is disclosed in which the solution being studied is retained around the working electrode and separated from the electrolyte by an annular piece of a current conducting membrane. The membrane is preferably an ion selective membrane, preferably Nafion, a copolymer of tetrafluoroethylene and a vinylsulfonyl fluoride.

18 Claims, 7 Drawing Figures

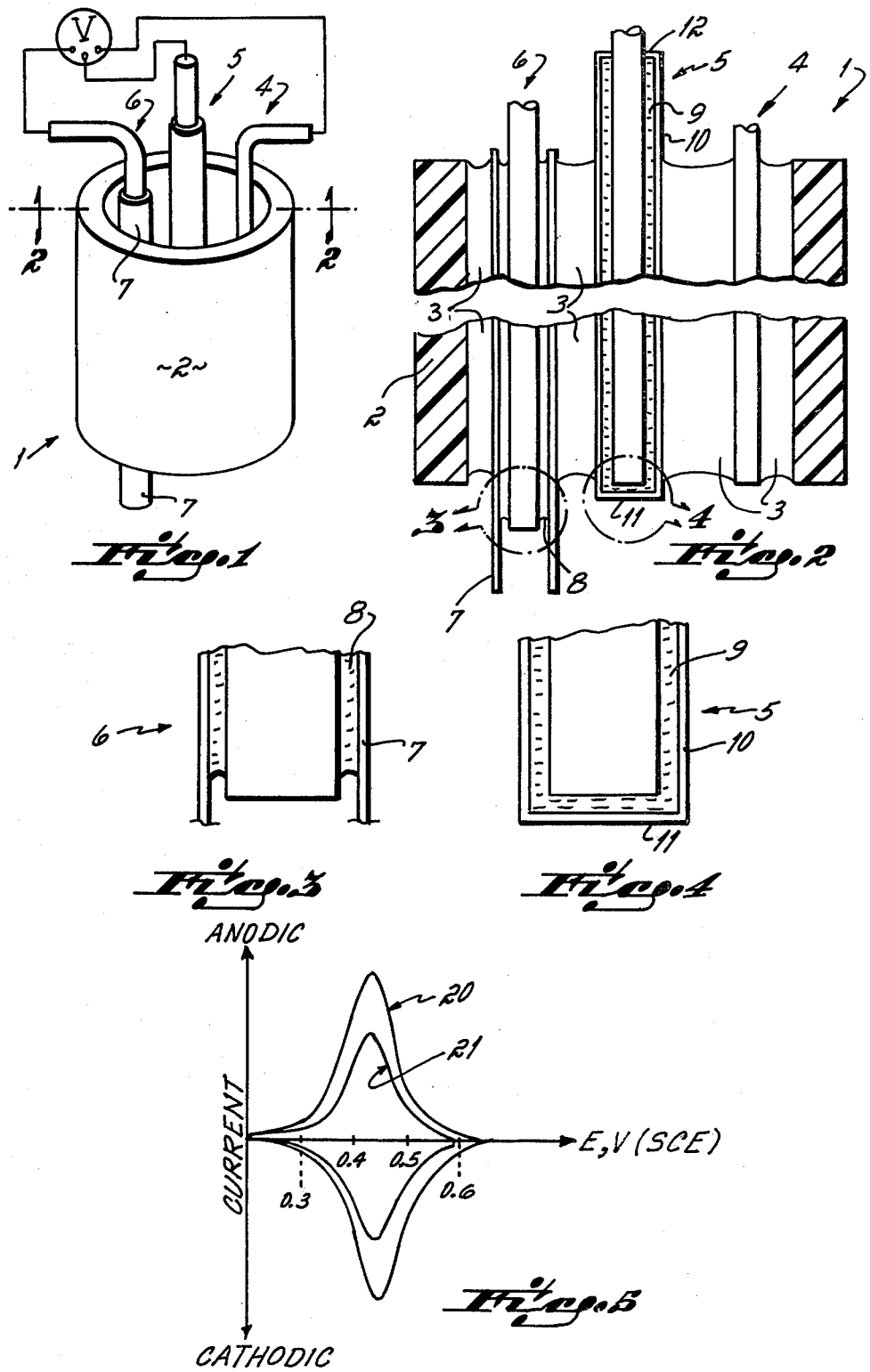

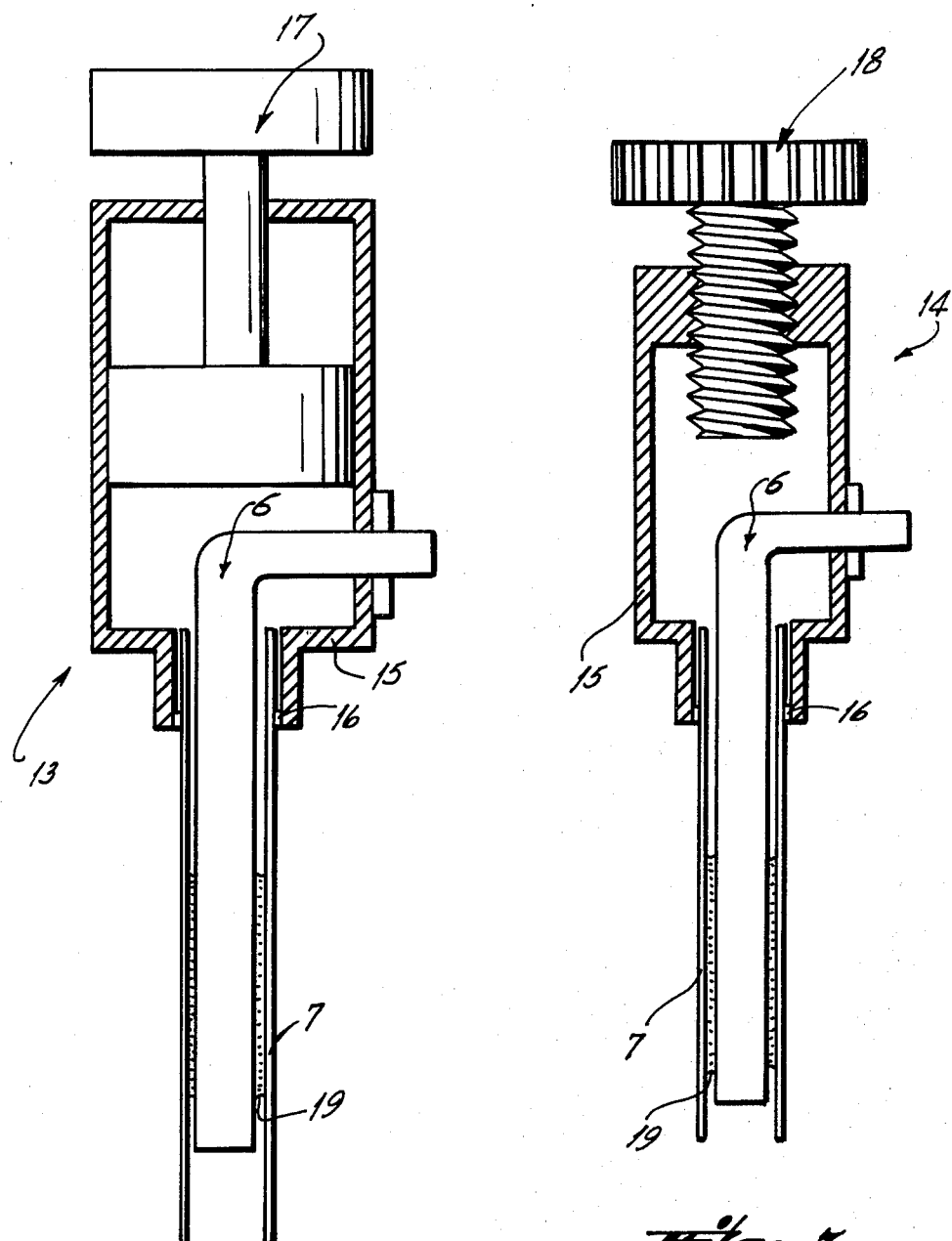

THIN LAYER ELECTRODE AND CELL

BACKGROUND OF THE INVENTION

This invention concerns the electrochemical analysis of liquids. More particularly, this invention discloses a novel electrochemical cell which permits the electrochemical analysis of extremely minute amounts of liquid, i.e., 0.25 to 1.0 $\mu$l.

Methods have been developed from the electrical analysis of thin layers of liquids. These devices, generally referred to as thin layer electrodes, have taken various forms such as micrometer-based electrode systems, "capillary" wire electrodes, dip-type thin layer electrodes, conducting glass cells and thin metal-film sandwich electrodes. In general, the thin layer electrodes and cell designs are either expensive and difficult to construct or require unusual manipulative techniques. Furthermore, although some of the thin layer electrode cells are specifically designed to use only a small amount of electroactive substance (volumes on the order of 1 micro liter), ohmic polarization usually limits their applicability to routine use. This ohmic polarization causes distortion of the electrochemical response curves. These limitations become very pronounced with poorly conducting or diluted electrolytes and high reactant concentration.

Thus, it is the object of this invention to disclose an electrode and an electrolytic cell for use in studying liquids requiring only a minute amount of said investigate liquid, i.e., between 0.25 $\mu$l to 1.0 $\mu$l.

In addition, it is the purpose of this invention to provide such an electrolytic cell in which the distortion effects caused by ohmic polarization are minimized even with diluted electrolytes and high reactant concentration.

Furthermore, it is the object of this invention to disclose a thin layer electrode with the advantages mentioned above which is inexpensive to produce.

SUMMARY OF THE INVENTION

The present invention consists of a simple, inexpensive wire thin layer electrode and electrolytic cell in which a current-conducting semipermeable membrane is used as a separator.

DESCRIPTION OF THE DRAWINGS

FIG. 1 is a diagrammatic perspective view of the invention;

FIG. 2 is a cross-sectional view of the invention taken along line 2—2 of FIG. 1;

FIG. 3 is a fragmentary blown-up view of the section of the invention enclosed in circle 3 of FIG. 2;

FIG. 4 is a fragmentary blown-up view of the section of the invention enclosed in circle 4 of FIG. 2;

FIG. 5 is a graph showing data collected using this invention;

FIG. 6 is an alternate embodiment of the invention; and

FIG. 7 is a second alternate embodiment of the invention.

DETAILED DESCRIPTION OF THE INVENTION

This invention consists of an electrolytic cell 1 which preferably is a piece of Teflon tubing 2 open at both ends containing an electrolyte 3 and three electrodes. The three electrodes consist of an auxiliary electrode 4, a reference electrode 5 and a working electrode 6.

These electrodes are preferably thin (a fraction of a millimeter in diameter) metal wires, preferably a substantially inert metal such as gold or platinum. Surrounding the working electrode 6 is a membrane 7. This membrane is open at either end and permits investigate fluid 8 to enter and be held around the working electrode 6 by means of capillary action. In addition, the membrane acts to separate the fluid 8 from the electrolyte 3.

Surrounding the reference electrode 5 is a layer of electrolyte 9 which is surrounded and retained in place by a membrane 10 which is substantially identical in chemical composition to the membrane 7 surrounding the working electrode. The membrane 10 which surrounds the reference electrode is preferably heat sealed at both ends 11 and 12 so that the electrolyte 9 is permanently retained in position around the electrode.

The electrolyte 9 surrounding the reference electrode and the electrolyte 3 within the electrolytic cell are preferably the same solution in order to compensate for the reaction of the electrolyte as current is applied through the cell.

In operation, the three electrodes are positioned within the Teflon sleeve 2. For purposes described below, the membrane 7 surrounding the working electrode should extend below the bottom of the working electrode as shown in FIG. 2, and both the electrode and the membrane should extend below the bottom of the Teflon tube, also as shown in FIG. 2.

An electrolyte solution selected from a vast selection of electrolytes which are well known to those skilled in the art is drawn into and retained with the Teflon sleeve by capillary action. The investigate solution 8 is then placed in contact with the bottom of the membrane 7 surrounding the working electrode 6. Capillary action draws this solution up and around the working electrode forming a thin layer between the working electrode and the membrane. The volume of this thin layer varies depending on the length of the wire, but can easily be empirically determined by means of chronocoulometry. As described above, the membrane surrounding the reference electrode is sealed at both ends 11 and 12.

The membranes which surround the working and reference electrodes are critical to the proper functioning of this invention. This membrane material must be one which restricts the flow of the investigate substance, (as well as the electrolyte) thus, preventing its mixture with the electrolyte, yet one which permits the flow of current. Such membranes are well known and frequently are ion selective, i.e., permitting only the flow of cations or anions.

The preferred membrane for use in this invention is Nafion, a copolymer of tetrafluoroethylene and a vinyl sulfonyl fluoride produced by E. I. duPont de Nemours & Co., Inc. Nafion, because of its cationic permeability has very low ohmic resistance and, therefore, does not exhibit significant distortion in the electrochemical response even with relatively fast transient experiments.

Because of the cationic permeability and small porosity of this material, electroactive anions and larger neutral and cationic species (Vitamin $B_{12a}$ and $B_{12}$, for example) have an immeasurable rate of diffusion out of the thin layer electrode assembly during the course of the typical electrochemical experiments. Small cations such as $Fe^{+3}$ are taken up by the membrane and, therefore, cannot be used with this membrane.

Other selective current-conducting membranes can be substituted for Nafion and can be readily selected by one who is skilled in the art.

FIG. 6 and FIG. 7 show two alternate constructions of this invention. As previously mentioned, the investigate liquid can be drawn around the working electrode 6 by capillary action. By use of the assemblies shown in either FIG. 6 or FIG. 7, a controlled amount of investigate solution can be drawn around the working electrode.

Both alternate embodiments 13 and 14 have a chamber 15 through which the working electrode 6 passes. The chamber is substantially air tight except for the space between the membrane 10 and the electrode 6. Preferably, wax is used at 16 to create an air tight seal between the membrane and the atmosphere.

As seen in FIG. 6, assembly 13 contains a plunger 17 in hermetic relationship with the walls of chamber 15. By pulling plunger 17, a partial vacuum is created in chamber 15, which in turn causes liquid to be drawn up and around the working electrode.

The assembly 14 shown in FIG. 7 is basically the same as assembly 13 with the exception that plunger 17 of assembly 13 is replaced by a screw 18. Screw 18 is also in hermetic relationship with said chamber 15. By turning the screw outwardly, the volume of chamber 15 increases, thus creating a partial vacuum. This, in turn, draws investigate liquid around electrode 6.

When using assemblies 13 or 14, any vessel may be used to hold the three electrodes of the cell (i.e., the working electrode, reference electrode, and auxiliary electrode); and, the open ended tube described previously is not required. The working electrode can be simply dipped into the electrolyte without permitting the electrolyte and the investigate liquid from mixing. This is accomplished by drawing air within the area between the membrane 10 and the electrode 6 and below the investigate liquid as shown at 19. This air pocket effectively prevents mixing of the investigate liquid and the electrolyte. Therefore, by using assemblies 13 or 14, one can dip the thin layer electrode into the electrolyte. Use of these assemblies also gives more control when drawing the investigate liquid around the electrode.

EXAMPLE

A thin layer cell using Nafion as the membrane material was constructed as previously described. The investigate substance was 0.25 μl of 10 mM $Fe(CN)_6^{-4}$ which was subsequently oxidized to $Fe(CN)_6^{-3}$ in the reverse sweep.

The results are shown in FIG. 5 in which curve 20 is obtained using a sweep rate of 1 mv/sec and curve 21 is obtained with a 2 mv/sec sweep rate. The results are summarized in Table 1.

TABLE I

| | .25 μl $Fe(CN)_6^{-3}$ | |
| --- | --- | --- |
| Sweep Rate | ΔE(ip/2) | Δ(Epa - Epc) |
| 1mv/sec | 90 mv | 10 mv |
| 2mv/sec | 102 mv | 20 mv |

Epa - potential at voltametric peak for cathodic scan
Epc - potential at voltametric peak for anodic scan
ΔE - voltage between electrodes in two electrode ampermetry
ip - peak current Thin layer electrode theory predicts that the peak potentials for the forward and reverse scans for reversible reactions are the same and that the half peak potentials are 90 mv. Note that the peak potentials in curve 20 do have a slight separation and the half peak widths do slightly exceed the theoretical values. These deviations are scan rate dependent as shown, and result from the finite resistance of the Nafion membrane separator. These deviations can be reduced, but, of course, not eliminated by using a gold minigrid auxiliary electrode mounted concentric to the thin layer electrode assembly.

From the foregoing description, it will be apparent that the invention disclosed herein provides a greatly improved thin layer electrode. As will be understood by those familiar with the art, the invention may be embodied in other specific forms, such as forms using other membranes with similar characteristics to Nafion as generally described by W. Grot in 44 Chem-Ing-Tech. 167 (1972) and 47 Chem-Ing-Tech. 617 (1975) and 50 Chem-Ing-Tech. 299 (1978). Such changes would not depart from the spirit or essential characteristics of this invention.

We claim:

1. A thin layer electrode comprising an electroconductive element and an ion exchange membrane in spaced relation to said element, said membrane being positioned in relation to said element in such a manner so as to be capable of retaining a thin layer of investigate liquid between said element and said membrane, said membrane also acting as an electrolyte separator, and means to admit said investigate liquid between said membrane and said electro-conductive element.

2. A thin layer electrode according to claim 1 in which said electro-conductive element is a wire and said membrane is a tubular membrane surrounding said wire and open at both ends.

3. A thin layer electrode according to claim 1 in which said membrane is an ion selective permeable membrane.

4. A thin layer electrode according to claim 3 in which said membrane is formed from a copolymer of tetrafluoroethylene and a vinyl sulfonyl fluoride.

5. A thin layer electrode according to claim 1 where said investigate liquid is maintained between said element and said membrane by capillary action.

6. A thin layer electrode cell comprising a working electrode, a reference electrode and an auxiliary electrode and a vessel for retaining said electrodes and an electrolyte wherein said working electrode and said reference electrode each consists of an electro-conductive element and an ion exchange membrane in spaced relation to said element said membrane being positioned in such a manner as to be capable of retaining a thin layer of liquid between said element and said membrane, means to admit liquid between said element and said membrane, said membrane also acting as an electrolyte separator.

7. A thin layer electrode cell according to claim 6 in which said electro-conductive elements are wires and said membranes are tubular membranes surrounding said wire elements.

8. A thin layer electrode cell according to claim 7 in which said tubular membrane surrounding said reference electrode is sealed at both ends.

9. A thin layer electrode cell according to claim 7 in which said membrane surrounding said working electrode is open at both ends and extends beyond the bottom of said wire.

10. A thin layer electrode cell according to claim 6 in which said membrane is an ion selective permeable membrane.

11. A thin layer electrode cell according to claim 10 in which said ion selective permeable membrane is a copolymer of tetrafluoroethylene and a vinyl sulfonyl fluoride.

12. A thin layer electrode cell according to claim 7 in which said vessel consists of a tube open at both ends, the length of said tube being less than the length of the membrane surrounding said wire in said working electrode, the width of said tube being such that liquid can be held within the tube by capillary action.

13. A thin layer electrode according to claim 1 including a means to draw liquid between said element and said membrane.

14. A thin layer electrode according to claim 13, wherein said means to draw liquid between said element and said membrane consists of a chamber hermetically sealed to one end of said membrane in combination with a means to increase the internal volume of said chamber.

15. A thin layer electrode according to claim 14 wherein said means to increase the internal volume of said chamber is a screw hermetically positioned into said chamber and capable of adjusting the volume of said chamber by rotating relative to said chamber.

16. A thin layer electrode cell comprising a vessel and three electrodes including a working electrode, a reference electrode and an auxiliary electrode within said vessel wherein the working and reference electrodes are surrounded by a membrane formed from a copolymer of tetrafluoroethylene and a vinyl sulfonyl fluoride; the membrane surrounding said reference electrode is sealed at both ends; wherein said membrane surrounding said working electrode is positioned in relation to said working electrode in such a manner so as to be capable of retaining a thin layer of investigate liquid between said working electrode and said membrane; and said vessel is a tube opened at both ends, the length of which is less than the length of the membrane surrounding the working electrode, the width of said tube being such that the liquid can be retained within said tube by capillary action.

17. An electrode comprising an electro-conductive element and an ion exchange membrane in spaced relation to said electroconductive element, said membrane being positioned in relation to said element in such a manner so as to be capable of retaining a thin layer of investigate liquid between said element and said membrane, said membrane also acting as an electrolyte separator, wherein said electro-conductive element is a wire and said ion exchange membrane is a tubular membrane surrounding said wire and open at both ends.

18. An electrode cell comprising a working electrode, a reference electrode and an auxiliary electrode in a vessel for retaining said electrodes and electrolyte wherein said working electrode and said reference electrode each consists of an electroconductive element and an ion exchange membrane in spaced relation to said element, said membrane being positioned in such a manner as to be capable of retaining a thin layer between said element and said membrane, said membrane also acting as an electrolyte separator, wherein said electroconductive elements are wires and said membranes are tubular membranes surrounding said electro-conductive elements and wherein at least one tubular membrane is open at both ends and extends beyond the bottom of said electro-conductive element.

* * * * *